United States Patent [19]

Stoner et al.

[11] 4,135,494

[45] Jan. 23, 1979

[54] OVER-PRESSURE PROTECTION DEVICE

[75] Inventors: David L. Stoner, College Station; Charles F. Shield, III, San Antonio; Ronald G. Julian, San Antonio; Ewald Koegel, San Antonio, all of Tex.

[73] Assignee: The United States of America as represented by the Secretary of the Air Force, Washington, D.C.

[21] Appl. No.: 776,038

[22] Filed: Mar. 9, 1977

[51] Int. Cl.² ............................................. A61B 19/00
[52] U.S. Cl. ...................................... 128/1 R; 3/1.4; 73/731
[58] Field of Search ............ 128/1 R, 2.05 D, 2.05 E, 128/214 F, 349 BU, DIG. 12; 3/1.4; 73/405, 406

[56] References Cited

U.S. PATENT DOCUMENTS

| 3,610,230 | 10/1971 | Anderson | 128/2.05 D |
| 3,625,199 | 12/1971 | Summers | 128/2.05 D |
| 3,710,777 | 1/1973 | Sparks | 128/1 R |
| 3,794,043 | 2/1974 | McGinnis | 128/349 BU |
| 3,916,874 | 11/1975 | Perrin | 128/1 R |
| 3,958,557 | 5/1976 | Sharp et al. | 3/1.4 |
| 4,000,741 | 1/1977 | Binard et al. | 128/349BU |
| 4,050,893 | 9/1977 | Hancock et al. | 3/1.4 |

Primary Examiner—Robert W. Michell
Assistant Examiner—Henry S. Layton
Attorney, Agent, or Firm—Joseph E. Rusz; Jacob N. Erlich

[57] ABSTRACT

An over-pressure protection device utilized for limiting the fluid pressure applied to a vein which has been removed from the body and which is being tested prior to transplantation within the body. The over-pressure protection device has a port for accepting a fluid under pressure, a tapered fitting for connection of the device to the vein to be tested and a resilient membrane which regulates the pressure of the fluid being applied to the vein. The specific characteristics of the resilient membrane limits the fluid pressure applied to the vein and therefore prevents subsequent deterioration of the vein.

2 Claims, 2 Drawing Figures

OVER-PRESSURE PROTECTION DEVICE

STATEMENT OF GOVERNMENT INTEREST

The invention described herein may be manufactured and used by or for the Government for governmental purposes without the payment of any royalty thereon.

BACKGROUND OF THE INVENTION

This invention relates generally to devices which prevent over-pressurization, and, more particularly to a device which prevents the over-pressurization of vein segments during preparation for grafting.

Autogeneous venous bypass grafts have been accepted as a technique for arterial reconstructive surgery. Originally this graft found use as a conduit to circumvent atherosclerotic occlusive disease in the superficial femoral artery. In more recent times, however, they have also been employed as conduits from the aorta to the distal coronary arteries for coronary artery insufficiency. As more fully explained in Vol. 76, No. 6, pp 1033-1040 of SURGERY dated December 1974, it has become increasingly apparent that venous bypass grafts undergo a substantial loss of patency with time. In fact, veins grafted into the aorta-to-coronary artery position were found to undergo a degenerative process emerging as a subintimal fibrous hyperplasia.

A possible factor involved in the cause of the problem set forth hereinabove are the changes that are induced in the veins used in the graft by methods and apparatus heretofore in use for the preparation of the vein segment prior to the insertion of the vein into the arterial circulation.

Presently, in the preparation of veins for the abovementioned grafting procedure, distention of the vein is required to localize potential bleeding points so that ligation of these points can be obtained prior to insertion of the graft. During this preparatory procedure a medical syringe is tied directly to the removed vein and a saline solution is injected therein at an arbitrary pressure. Unfortunately, in many instances, this pressure exceeds 500mm/hg and depends upon the rate of injection and skill of the surgeon administrating the saline solution.

It has been shown that such resultant high hydrostatic forces acting upon the vein disrupt the integrity of the intima and media of the vein wall resulting in subsequent failure of the grafted segment from progressive fibrosis and internal hyperplasia.

SUMMARY OF THE INVENTION

The instant invention sets forth an over-pressure protection device which overcomes the problem set forth hereinabove by preventing hydrostatic forces from being delivered to the vein segment above a preset level.

The over-pressure protection device of this invention is in the form of a three port housing having a resilient membrane connected to a pressure port located at one end thereof. One of the other two ports, which is located on the side of the housing, accepts a syringe for the application of a saline solution to the vein segment while the remaining opening at an opposite end of the housing to the pressure port has a tapered end fitting operatively connected to the vein segment to be utilized in the arterial reconstruction.

In use, the over-pressure protection device has its tapered fitting inserted within the excised vein (generally the saphenous vein). The other end of the excised vein is then clamped by any conventional medical procedure. The resilient member of desired thickness and pressure regulating characteristics is placed over the pressure port and secured in place. A saline-filled syringe is then inserted in the side opening and enough saline solution is injected to distend the resilient membrane. Distention of the resilient member assures that the desired pressure is being exerted against the walls of the vein under test.

The pressure applied to the vein is dependent upon the characteristics of the resilient membrane. The rate of injection of the saline solution will not affect the pressure profile applied to the vein as the membrane will absorb the shock of a "high rate" injection and as a result thereof, the over-pressure protection device of this invention will apply pressure evenly to the vein.

It is therefore an object of this invention to provide an over-pressure protection device which is extremely useful in the prevention of vein damage during the pressure checks of veins used in coronary artery by-pass operations.

It is a further object of this invention to provide an over-pressure protection device which will prevent hydrostatic forces from being delivered above a preset level.

It is still another object of this invention to provide an over-pressure protection device which is economical to produce, extremely reliable in operation and which utilizes conventional, currently available components in the manufacture thereof.

For a better understanding of the present invention together with other and further objects thereof reference is made to the following description taken in conjunction with the accompanying drawing and its scope will be pointed out in the appended claims.

DETAILED DESCRIPTION OF THE PREFERRED EMBODIMENT

Figure 1:
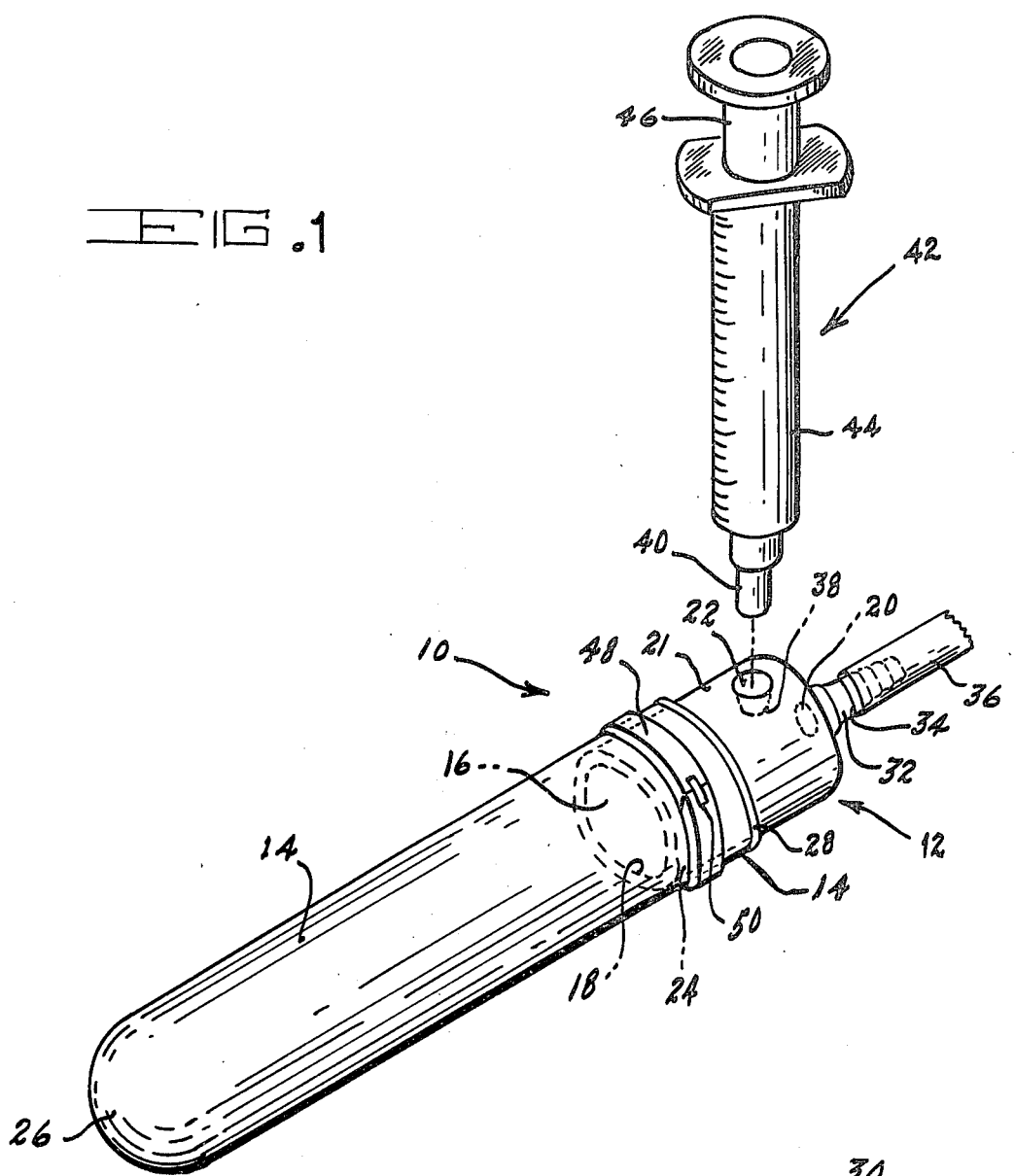
FIG. 1 of the drawing is a pictorial representation of the over-pressure protection device of this invention in position of use within an excised vein.

Reference is now made to FIG. 1 of the drawing which pictorially represents the over-pressure protection device 10 of this invention. Over-pressure protection device 10 is made up of a housing 12 and a pressure regulating means defined by membrane 14. Housing 12 is made of any suitable material such as plastic and has a hollow interior portion 16. Although preferably of cylindrical configuration, housing 12 may be of any other suitable shape.

Housing 12 has three ports 18, 20 and 22 located therein. Ports 18, 20 and 22 are all operatively connected to hollow interior 16 of housing 12. Port 18 is located at one end of housing 12 and although not limited to a specific diameter preferably has an inner diameter of 0.5 inches. The outer diameter of port 18 which forms part of housing 12 terminates in a tapered segment 24. Segment 24 inserts within any of a plurality of pressure regulating membranes 14.

Figure 2:
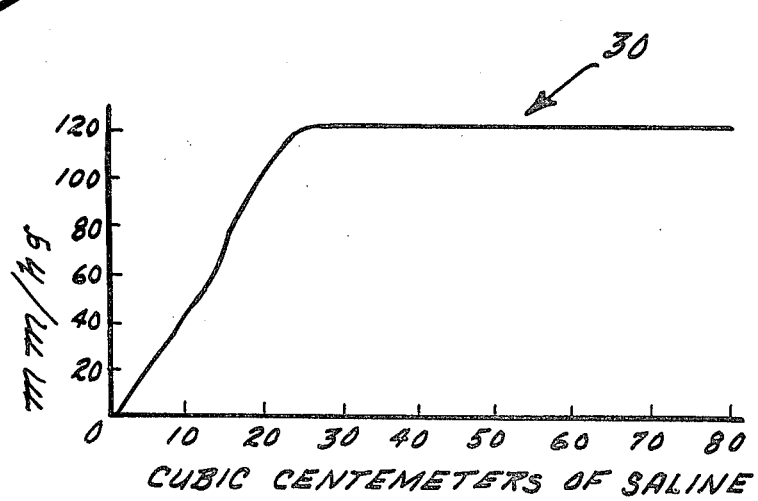
FIG. 2 of the drawing is a graph representing the pressure versus volume curve of the resilient membrane utilized with the over-pressure protection device of this invention.

Pressure regulating membrane 14 is preferably in the form of an elongated resilient membrane made preferably of rubber or other suitable resilient material closed at one end 26 and open at the other end 28. Membrane 14 determines the static pressure of device 10. As a result thereof, the pressure emanating from port 20 does not exceed the pressure applied to membrane 14. The resilient rubber membrane 14, for optimum results, should have a pressure versus volume curve as shown in graph 30 of FIG. 2 of the drawing. The variance from the data supplied with FIG. 2 should not be greater than ±10%. In addition, membrane 14 should have a capacity of approximately 80cc of liquid.

Port 20 of housing 12 terminates in a tapered, male fitting 32 having a plurality of grooves 34 thereon. Although capable of having a variety of sizes, fitting 32 is preferably of a 0.125 inch inner diameter and approximately 0.5 inches in length. Fitting 32 may either be of integral construction with housing 12 or be a separate element secured thereto by any suitable securing means such as glueing. The outer diameter of fitting 32 should be small enough to be inserted within a vein 36 to be tested.

Located in a side wall 21 perpendicular to the longitudinal axis of housing 12 is port 22. Port 22 is of a tapered internal configuration 38 and designed to readily accommodate the end 40 of any conventional medical syringe 42 having body 44 and plunger 46. Although syringe 42 is preferably removeable from housing 12, it may, if desired, be permanently attached to housing 12 having end 40 fixedly secured within port 22. Any suitable fluid such as saline solution is filled within body 44 of syringe 42 for use with over-pressure protection device 10 of the instant invention. Best results are obtained with the utilization of a 50cc syringe 42 although this invention is not limited thereto.

In operation, over-pressure protection device 10 has its tapered fitting 32 inserted within an excised or removed vein 36 (preferably the saphenous vein) prior to the grafting operation. Vein 36 is connected to the tapered, grooved fitting 32 of device 10 by any suitable securing method such as tying thereto with a surgical suture material. The open end (not shown) of vein 36 is closed with suture material or a suitable medical clamp.

The appropriate rubber membrane 14, as prescribed by graph 30, is secured to segment 24 of housing 12 by any suitable removeable securing means such as clamp 48 having catch 50 thereon. If syringe 42 is attached to housing 12, a saline solution is filled within syringe 42, if syringe 42 is an independent element, a saline solution-filled syringe 42 is inserted within tapered port 22 until a tight fit is secured.

As the saline solution is slowly forced into the hollow interior 16 of housing 12 the pressure thereof is slowly distributed equally against membrane 14 and vein 36. Since the static pressure is regulated by membrane 14, the pressure applied to vein 36 will not exceed the pressure applied to membrane 14. For optimum performance of over-pressure prevention device 10 of this invention the variance from the data shown in FIG. 2 of the drawing should not exceed ± 10%. Enough saline solution should be injected into housing 12 so as to distend membrane 14. This distention of membrane 14 assures that the appropriate pressure is exerted against the walls of vein 36.

With the use of device 10 of this invention sufficient distention of vein 36 occurs for proper checking of vein 36 before vein 36 is inserted during the grafting operation. Any hydrostatic forces above a preselected level are prevented from damaging vein 36. As a result of the use of the instant invention, many of the failures previously associated with failure of the intima and media of the vein walls have been eliminated.

Although this invention has been described with reference to a particular embodiment, it will be understood to those skilled in the art that this invention is capable of a variety of alternate embodiments within the spirit and scope of the appended claims.

We claim:

1. An over-pressure protection device for use in the pressure testing of veins comprising a housing, said housing having a hollow interior configuration, a first port of predetermined diameter located in said housing, said first port being coincidental to the longitudinal axis of said housing and operably connected to said hollow interior thereof, a tapered male fitting connected to said housing and in operative alignment with said first port, said tapered male fitting being capable of operative connection to an end of said vein, a second port located in said housing, said second port being situated perpendicular to the longitudinal axis of said housing and operably connected to said hollow interior thereof, said second port being capable of operative connection to means for delivering a fluid under pressure to said hollow interior of said housing, a third port having a diameter greater than said predetermined diameter located in said housing, said third port being coincidental with the longitudinal axis of said housing and operably connected to said hollow interior thereof and a pressure regulating means defined by an elongated resilient membrane removably connected to said housing and in operative relationship with said third port for regulating the pressure of said fluid emanating from said second port, said resilient membrane being capable of extending in a direction coincidental to the longitudinal axis of said housing whereby the pressure of said fluid emanating from said second port and being applied to said vein is limited by the characteristics of said elongated resilient membrane.

2. An over-pressure protection device as defined in claim 1 wherein said third port has an inner diameter of approximately 0.5 inches and said first port has an inner diameter of approximately 0.125 inches.

* * * * *